(12) United States Patent
Branch et al.

(10) Patent No.: US 8,945,061 B2
(45) Date of Patent: Feb. 3, 2015

(54) OTIC FORMULATIONS, METHODS AND DEVICES

(71) Applicant: Entrx LLC, Corsicana, TX (US)

(72) Inventors: Matthew Branch, Corsicana, TX (US); Vance Oglesbee, Corsicana, TX (US)

(73) Assignee: Entrx LLC, Corsicana, TX (US)

( * ) Notice: Subject to any disclaimer, the term of this patent is extended or adjusted under 35 U.S.C. 154(b) by 42 days.

(21) Appl. No.: 13/733,727

(22) Filed: Jan. 3, 2013

(65) Prior Publication Data

US 2013/0178801 A1    Jul. 11, 2013

Related U.S. Application Data

(60) Provisional application No. 61/649,663, filed on May 21, 2012, provisional application No. 61/625,407, filed on Apr. 17, 2012, provisional application No. 61/585,031, filed on Jan. 10, 2012.

(51) Int. Cl.

| | |
|---|---|
| *A61M 5/00* | (2006.01) |
| *A01N 43/04* | (2006.01) |
| *A61K 31/70* | (2006.01) |
| *A61F 11/00* | (2006.01) |
| *A61K 31/496* | (2006.01) |
| *A61K 31/7048* | (2006.01) |
| *A61K 31/4174* | (2006.01) |
| *A61K 31/573* | (2006.01) |
| *A61K 31/27* | (2006.01) |
| *A61K 9/00* | (2006.01) |
| *A61K 47/06* | (2006.01) |
| *A61K 47/32* | (2006.01) |

(52) U.S. Cl.
CPC ............... *A61F 11/00* (2013.01); *A61K 31/496* (2013.01); *A61K 31/7048* (2013.01); *A61K 31/4174* (2013.01); *A61K 31/573* (2013.01); *A61K 31/27* (2013.01); *A61K 9/0046* (2013.01); *A61K 47/06* (2013.01); *A61K 47/32* (2013.01)
USPC ............................................. 604/173; 514/31

(58) Field of Classification Search
CPC ............ A61K 2300/00; A61K 31/573; A61K 9/0046; A61K 2039/54
See application file for complete search history.

(56) References Cited

U.S. PATENT DOCUMENTS

| | | | |
|---|---|---|---|
| 7,220,431 | B2 | 5/2007 | Sawchuk et al. |
| 8,030,297 | B2 | 10/2011 | Lichter et al. |
| 2006/0194769 | A1* | 8/2006 | Johnson et al. ............... 514/114 |
| 2007/0078116 | A1* | 4/2007 | Lane ............................. 514/171 |
| 2010/0036000 | A1* | 2/2010 | Lichter et al. .............. 514/772.1 |
| 2011/0251147 | A1 | 10/2011 | Venkatesh |

FOREIGN PATENT DOCUMENTS

WO   PCT/US2013/020152     3/2013

OTHER PUBLICATIONS

Petrou, M. A. et al. In-vitro Activity of Antifungal Agents in Combination with Four Quinolones, Drugs Exptl. Clin. Res. 1988, XIV (1), 9-18.*

Arayan S, Swift A. Otitis externa: a clinical review. Br J Hosp Med (Lond). Oct. 2011;72(10):554-8.

* cited by examiner

*Primary Examiner* — Gina Justice
*Assistant Examiner* — Genevieve S Alley
(74) *Attorney, Agent, or Firm* — Boulware & Valoir (57) ABSTRACT

The present invention relates to a formulation and method for treating an ear infection, especially otomycosis and otitis externa, by administering a one-time only treatment comprising an antibiotic, and antifungal, and an anti-inflammatory in a thick, otic carrier. In one embodiment, the formulation comprises a therapeutically effective amount of active ingredients including a fluoroquinolone, a triazole antifungal, a thiocarbamate antifungal, a corticosteroid and a polyene antifungal, as well as a thickener such that the formulation, upon applying to the infected ear canal, gels and remains in the ear canal, continuously releasing the active ingredients for several days, achieving consistent complete (98-100%) clinical resolution of otomycosis and otitis externa in a single application.

20 Claims, 4 Drawing Sheets

OTIC FORMULATIONS, METHODS AND DEVICES

PRIOR RELATED APPLICATIONS

This application claims priority to 61/585,031, filed Jan. 10, 2012, 61/625,407, filed Apr. 17, 2012, and 61/649,663, filed May 21, 2012, and each incorporated by reference herein in its entirety.

FIELD OF THE INVENTION

The invention relates to an anti-fungal/anti-bacterial/anti-inflammatory formulation for treating ear infection, especially chronic otitis, and methods and devices for delivering the formulation.

BACKGROUND OF THE INVENTION

Ear infections, especially fungal ear infections, are common ear disorders often occurring in warm and humid climates. Fungal otitis externa is a fungal infection of the external auditory canal and associated complications. It has been reported that as high as 30.4% of otitis externa patients exhibit symptoms of fungal otitis or inflammatory conditions of the ear.

Common symptoms of ear fungal infection include otalgia, otorrhea, hearing loss, aural fullness, pruritus and tinnitus. Several factors that may cause or enhance the rate of fungal infection include humid climate, the presence of cerumen (ear wax) acting as a support for fungal growth, configuration of the ear canal, weak immune function, diabetes, increased use of ototopical antibiotics, prolonged use of broad-spectrum antibiotics, use of systemic steroids, pregnancy, hearing aids with occlusive molds, trauma and bacterial infections.

Common fungi that cause otitis externa are *Aspergillus niger* and *Candida albicans*, and treatment thereof can be tailored against these fungi. Other fungi may also cause otitis externa, and can also be treated by respective therapeutic agents. It is debatable whether identification of the causal agent is necessary for determining the appropriate treatment. One school of thought believes that the treatment should be based on the susceptibility of the identified species, whereas others believe that the treatment should based on efficacy and characteristics of the drug regardless of the causing microbes. An experienced Ear, Nose and Throat physician (ENT) can now routinely treat fungus without cultures, mostly by identifying the characteristic fungal elements grossly on exam, and apply topical acidifying agents or specific antifungals. Thus, practitioners can identify the organism, or just treat the likely organisms empirically according to best practices, as desired.

Currently, there are four main classes of drugs for the treatment of fungal infections, including polyenes, triazoles, nucleoside analogues and enchinocandins. The mechanism of action of the polyenes and triazoles families involves an essential chemical component called ergosterol found in the fungal cell membrane. The drug binds to ergosterol and creates a polar pore in the fungal membranes, which results in the leaking of ions and other molecules from within the cell, which in turn kills the cell. The nucleoside analogs interfere with nucleotide synthesis, which prevents proper energy production, metabolism and signaling of the cell. Echinocandins are a novel class of anti-fungal agents, acting by interfering with cell wall biosynthesis. However, echinocandins are known to be embryotoxic, and dose adjustment is required for patients having liver diseases.

To date, most reported treatment involves a solution, cream, powder or ointment to be topically applied multiple times for a period of time from one week to one month. See, e.g. Table 2 of Munguia et al., *Ototopical antifungals and otomycosis: A review*, International J. of Pediatric Otorhinolaryngology (2008) 72, 453-459. The prolonged treatment regimen causes inconvenience to the patients because either they have to visit a primary care physician or otolaryngologist multiple times, or for self-administered drugs, patients often forget to apply the drugs according to instruction, resulting in secondary proliferation of fungus and bacteria that may further extend the treatment period. In addition, many drugs do not have complete efficacy for infection caused by multiple agents, and this can again prolong treatment times. Moreover, pure liquid form of drugs, such as ear drops, are less desirable for treating chronic otitis externa especially because the liquids egress from the ear canal very rapidly, and not all infected areas within the ear canal can be reached by the liquid because of gravity, especially in the upper half of the ear canal. Creams and ointments, in contrast, often remain in the ear and then have to be removed by the ENT.

U.S. Pat. No. 7,220,431 discloses a method for administering a pharmacological agent to the middle ear of a mammal by applying a formulation to the tympanic membrane of the mammal. The method does not teach how to treat an infection occurred at the auditory canal, such as otitis externa. The formulation is characterized by having a viscosity of less than 100,000 cps, and the formulation forms a gel after application to the tympanic membrane. However, the practical application of this patent may be problematic because once the ear canal is occluded, additional ear drops cannot be introduced. In addition, the solidified gel can be hard to remove by the patients after the infection symptoms are resolved. If the solidified gel remains too long within the ear canal after releasing all the active ingredients, recurrence of fungal and bacterial infection is likely.

U.S. Pat. No. 8,030,297 discloses a method for treating otic disorders selected from Meniere's disease, autoimmune ear disease, otitis media, acoustic trauma induced sensorineural hearing loss, drug-induced sensorineural hearing loss, sensorineural hearing loss, idiopathic sensorineural hearing loss, vertigo, and tinnitus. The method requires intratympanic administration of a pharmaceutical composition comprising a thermoreversible aqueous gel having 16% to 21% by weight of polyoxypropylene and polyoxyethylene and from 1 mg/ml to 70 mg/ml of a multiparticulate anti-inflammatory corticosteroid. The "intratympanic" administration and the targeted disorders make it clear that this patent does not treat otitis externa. Also, the patent does not teach the use of any anti-fungal agent for treating fungal infection.

There are also a couple of veterinary products available for animal use. POSATEX OTIC SUSPENSION™ by Intervet®/Schering-Plough Animal Health® contains Orbifloxacin, Mometasone Furoate Monohydrate and Posaconazole in a suspension. However, it has limited efficacy (Pseudomonas aeruginosa and the yeast *Malassezia pachydermatis*) and the orbofloxacin is only approved for use in dogs. Further, it is required to be used daily for 7 consecutive days.

TRI-OTIC™ by Med-Pharmex® contains Gentamicin Sulfate, Betamethasone Valerate, and Clotrimazole. However, this formula too requires twice daily application into the ear canal for 7 consecutive days, and has limited efficacy (*Malassezia pachydermatis*, formerly *Pityrosporum canis*, and/or bacteria susceptible to gentamicin).

There are also a few combinations approved for use in humans, but all are of very limited efficacy. CIPRODEX® by Alcon® is 0.3% ciprofloxacin and 0.1 in a suspension (0.3% ciprofloxacin 0.1% dexamethasone). However, it has no efficacy against fungus, and is directed for twice daily use for seven days. CIPRO HC® is a similar formulation containing ciprofloxacin and hydrocortisone and has the same limitations. CORTISPORIN, available generically, contains neomycin and polymyxin B sulfates and hydrocortisone otic solution, but has the same limitations, and requires 3-4 applications a day for up to 10 days.

Therefore, there is still a need for a medical formulation and method for treating fungal ear infections, such as otomycosis and otitis externa, that requires only a single administration and yet is still capable of eradicating a spectrum of fungal and bacterial infections and the coincident inflammation. There is a particular need for a formulation that is capable of maintaining the active agents within the ear canal of a patient such that only a single dose of the formulation is required to achieve a high cure rate of otomycosis and otitis externa.

SUMMARY

The present disclosure relates to formulations, methods and devices for treating chronic otitis externa that requires only a one-time administration, while retaining very high efficacy against a broad spectrum of fungus and bacteria. The formulation comprises a therapeutically effective amount of one or more antibacterial agents, one or more antifungal agents, and one or more anti-inflammatory agents, together with a thickened base that egresses from the ear in less than 7 days.

Preferred embodiments include one, two or preferably all three of a triazole antifungal agent, a thiocarbamate antifungal agent, and a polyene antifungal agent. This can be combined with an antibacterial, such a fluoroquinolone antibiotic, and a corticosteroid anti-inflammatory agent. Together, these make up the active ingredients that eradicate a broad spectrum of fungal infections and any accompanying bacterial infection and inflammation. The formulation may also benefit from combination with anesthetics or analgesics. For example, benzocaine, which is already approved for otic use, can provide significant pain relief.

With the single-dose formulation of the present invention, complications due to patients' non-compliance in not following dosing instructions can be eliminated. Additionally, the optimal approach of applying the Active Pharmaceutical Ingredients ("APIs") directly to the infected area result in less bacterial community resistance due to a considerably lower one-time dose, thereby keeping bacterial resistance to a minimum.

Additionally, the use of a viscous carrier in the formulation makes it possible for the formulation to remain in viscous form once it is administered inside the ear canal and heated up by body temperature. Because of the high viscosity, the entire therapeutic formulation remains in contact with the infected ear canal for a prolonged time and the active ingredients can be continuously released for two to four days.

Exemplary formulations include:

TABLE A

Otic Formulations 0.01% fluoroquinolone, 0.1% triazole antifungal, 0.1% thiocarbamate, 0.01% corticosteroid, and 50,000 unit/ml of a polyene antifungal plus thickener and mineral oil.
1% fluoroquinolone, 2% triazole antifungal, 2% thiocarbamate, 1% by weight of a corticosteroid, and 200,000 unit/ml of a TABLE A-continued Otic Formulations polyene antifungal in thickener, and mineral oil.
0.3% ciprofloxacin, 1% clotrimazole, 1% tolnaftate, 0.1% dexamethasone; and 100,000 unit/ml of a nystatin in an otic carrier that is 10-25% wax, and 75-90% of mineral oil.
0.3% ciprofloxacin, 1% ofloxacin, 1% itraconazole, 1% tolnaftate, 0.1% dexamethasone, and 100,000 unit/ml of a nystatin in 10-25% wax and 75-90% mineral oil.
0.3% ciprofloxacin, 1% ofloxacin, 1% itraconazole, 1% tolnaftate, 0.1% dexamethasone, and 100,000 unit/ml of nystatin in 55-60% PCCA PlasticizedTM and 40-45% mineral oil.
0.3% ciprofloxacin, 1% ofloxacin, 1% clotrimazole , 1% tolnaftate, 0.1% dexamethasone, and 100,000 unit/ml of a nystatin in 55-60% PCCA PlasticizedTM and 40-45% mineral oil.
0.3% ciprofloxacin, ofloxacin, or the combination thereof, 1% by weight of a clotrimazole, itraconazole, or the combination thereof; 1% by weight of a tolnaftate; 0.1% by weight of a dexamethasone; and 100,000 unit/ml of a nystatin in an otic carrier that is 10-25% of wax; and 75-90% of mineral oil.
0.3% ciprofloxacin, 100,000 u/ml Nystatin, 1% Itraconazole, 0.1% Dexamethasone and 1% Tolnaftate in 18% candela wax and 82% mineral oil.
0.3% ciprofloxacin; 100,000 u/ml Nystatin, 1% clotrimazole, 0.1% Dexamethasone, 1% Tolnaftate (1% ) in 80% mineral oil and 20% bees wax.
0.3% ciprofloxacin; 100,000 u/ml Nystatin, 1% clotrimazole, 0.1% Dexamethasone, 1% Tolnaftate in 82% mineral oil and 18% paraffin.
0.3% ciprofloxacin; 100,000 u/ml Nystatin, 1% clotrimazole, 0.1% Dexamethasone, 1% Tolnaftate in mineral oil and wax.
0.3% ciprofloxacin; 1% clotrimazole, 0.1% Dexamethasone in 82% mineral oil and 18% paraffin.
0.5% ciprofloxacin; 2% clotrimazole, 0.2% Dexamethasone in 82% mineral oil and 18% paraffin.
0.6% ciprofloxacin; 2% clotrimazole, 0.2% Dexamethasone in 82% mineral oil and 18% paraffin.
0.3% ciprofloxacin, 100,000 u/ml Nystatin, 0.1% dexamethasone.
0.3% ciprofloxacin, 1% voriconazole, 0.1% dexamethasone.
0.3% ciprofloxacin, 1% amphotericin B, 0.1% dexamethasone.
0.3% levofloxacin, 1% amphotericin B, 0.1% dexamethasone.
0.3% levofloxacin, 1% voriconazole, 0.1% dexamethasone.
0.3% ciprofloxacin, 1% ketoconazole, 0.1% dexamethasone.
0.3% Ciprofloxacin; 1% clotrimazole, 0.1% hydrocortisone.

In another aspect of the invention, is the use of the herein described combination of compounds to manufacture a therapeutic to treat the herein described ear infections.

Another aspect of the invention, is a method of manufacturing a therapeutic agent, the method comprising blending the herein described combination of compounds together with a viscous carrier to make one of the herein described therapeutic compositions.

Another aspect of the invention is a kit comprising the herein described compositions packaged together with instructions for single administration use to treat ear infections.

Another aspect of the invention, is a kit comprising the herein described compositions packaged inside or with one of the herein described special syringes, together with instructions for single administration use to treat ear infections.

The single use otic formulation for the ear canal includes a viscous carrier. The carrier can be any ontologically acceptable materials with the desired viscosity and that achieves the goal of maintaining the formulation within the ear canal for a prolonged period of time, preferably at least 5 days. Choosing different carriers may change the physical nature of the formulation, but not the therapeutic effect. For example, a person skilled in the art may so choose the carrier to make the formulation in fluid, foam, cream, ointment, or other ontologically acceptable form.

Thickeners can be completely natural, like waxes, and also synthetic or semi-synthetic polymers and the like, including polysaccharides, proteins, alcohols, silicones or waxes. Suitable thickeners may include bees wax, candelilla wax, carnauba wax, paraffin, Ozokerite wax, cetyl alcohol, corn starch, glyceryl stearate, guar gum, gum Arabic, xanthan gum, lanolins, microcrystalline wax, acrylate polymers, poly-alphaolefins, HE-Cellulose, PEG-150 Distearate, sorbitol, stearic acid, stearyl palmitate, Poloxamer 407, and the like.

The preferred thickeners are water insoluble or have low water solubility for longevity, and are not ototoxic. Preferred carriers include a combination of mineral oil and thickener, such as the proprietary blend of low density polyethylene known as PCCA Plasticized™ (PCCA US, TX, Cat. No. 30-3211). Even more preferred is a blend 10-25%, 15-21% or 18% United States Pharmacopoeia (USP) or National Formulary (NF) paraffin brought to 100% (ww) with USP or NF mineral oil.

The carrier is characterized in that it remains a thick fluid in the preferred embodiment for human patients having approximately 60,000 cPs after being applied to a subject's ear canal and heated by the body temperature of 37° C. At least 40,000 cPs thickness is desired, preferably at least 50,000 or 60,000 cPs, however, variations can be accommodated. If the formulation is too thick, it will not egress, and thus formulations over 80,000 cPs are less desirable, and preferably less than 70,000 cPs. The dynamic A (absolute) viscosity is to be ascertained at 37° C. according to ATSM D-2394.

Although thick, the formulation remains a flowable fluid that can be applied by an injection unit, such as a syringe and a needle. The viscous fluid stays within the ear canal and remains in contact with the infected portion of the tissue. This allows the active ingredients within the formulation to be continuously released for a prolonged period of time, preferably at least 3 days, more preferred at least 4 days, and ideally 5 days, or even 6-7 days, thus continuously treating the fungal and bacterial infections, as well as the inflammation accompanied with the infections. More to the point, since the thick fluid will be in place for a prolonged period of time, the continuously released active ingredients will also maintain the hygiene within the ear canal by preventing the proliferation of fungi and bacteria. Additionally, the viscous nature of the formulation allows it to gradually egress from the ear canal (or be absorbed) after symptoms are resolved.

In a different embodiment of the invention, however, the carrier can be a thinner liquid formulation and the formulation used to treat of acute otitis media using tympanostomy tubes (AOMT). This would allow the use of a liquid form of the product to cross the tympanic membrane through a myringotomy tube in cases of ear drainage. Such carriers are described, for example in U.S. Pat. No. 7,220,431 and U.S. Pat. No. 8,030,297. However, some drugs suitable for use in the external ear canal may not be suitable for use across the membrane, and each will have to be tested for suitability.

Another aspect of the invention provides a method for treating an ear infection. The method comprises the step of applying, typically only once or possibly twice, a formulation into the ear canal of a mammal, wherein the formulation is as described herein.

In yet another aspect of the present invention, a therapeutic kit for treating ear infections is provided, comprising an injection unit having a storage compartment fluidly coupled to a delivery component, such as a small tube or syringe, and a therapeutic formulation stored within the storage compartment. The therapeutic formulation is as described herein. The device is preferably a single use device, disposed of after use. In other embodiments, the storage compartment allows for multiple doses, but the delivery component is disposable.

In particular preferred embodiments, the delivery component is a specially designed needle or semi-rigid cannula with about a 5-10 degree bend, or other angle as required, for reaching the desired location in the ear, and the end of the needle is rounded and smooth. The needle can be a metal standard needle that is bent and rounded during manufacture, but is preferably a soft flexible plastic needle with the rounded tip. In particularly preferred embodiments, the tip ends can curve inwards so that the user is presented with a smoothly rounded outer surface that is much less likely to scratch delicate ear tissues. The needle portion can also be a combination of metal and plastic, but a simple plastic device constructed by injection molding is likely to be the most cost effective design. In other preferred embodiments, the distal portion of the needle or tube is of a softer plastic (or is thinner) than the proximal portion. Thus the practitioner can have good control over needle movement, but the last cm or so of tip is very soft, further reducing the danger to ear tissues.

As used herein, "ear infection" means fungal and/or bacterial infection in the ear. The location of the infection is primarily the auditory canal. In a preferred embodiment, the term ear infection includes otomycosis, chronic and acute otitis externa.

As used herein, "active ingredient" means the substance of a pharmaceutical drug that has therapeutic effect against the disorder to be treated.

As used herein, "fluoroquinolone" means the class of fluoroquinolone antibiotics generally bearing the following chemical structure:

wherein R can be the same or different functional groups. Examples of fluoroquinolone that can be used in the present invention include, but are not limited to, ciprofloxacin, ofloxacin, levofloxacin, gatifloxacin, moxifloxacin, gemifloxacin, norfloxacin, danofloxacin, difloxacin, enrofloxacin, ibafloxacin, marbofloxacin, orbifloxacin, sarafloxacin, and combinations thereof.

As used here, "triazole antifungal" means either one of a pair of isomeric chemical compounds with molecular formula $C_2H_3N_3$, which has a five-membered ring of two carbon atoms and three nitrogen atoms. The pair of isomers have the following general structure:

Triazoles are synthetic agents that can reduce the concentration of ergosterol, which is essential in normal cytoplasmic membrane of fungus. Examples of triazole antifungals that can be used in the present invention include, but not limited to, clotrimazole, ketoconazole, itraconazole, fluconazole, miconazole, econazole, butoconazole, oxiconazole, sulconazole, terconazole, and combinations thereof.

As used herein, "thiocarbamate antifungal" means a family of organosulfur compounds that have the following general formula:

Examples of thiocarbamate antifungals that can be used in the present invention include, but are not limited to, tolnaftate and tolciclate, and combinations thereof. Tolnaftate acts by distorting hyphae and inhibiting the mycelial growth of susceptible fungi that cause skin infections, and has been recommended in refractory cases of otomycosis. It has been shown to be non-ototoxic.

As used herein, "corticosteroid" means a class of steroids having anti-inflammatory effect that may include, but are not limited to, amcinonide, betamethasone benzoate, betamethasone dipropionate, betamethasone valerate, clobetasol propionate, clocortolone pivalate, desonide, desoximetasone, dexamethasone, dexamethasone sodium phosphate, diflorasone diacetate, fluocinonide, fluocinolone acetonide, flurandrenolide, fluticasone propionate, halcinonide, halobetasol propionate, hydrocortisone, hydrocortisone butyrate, hydrocortisone valerate, mometasonefuroate, prednisolone acetate, triamcinolone acetonide, and combinations thereof.

As used herein, "polyene antifungal" means a macrocyclic polyene with a heavily hydroxylated region on the ring opposite the conjugated system, and examples of polyene antifungal that can be used in the present invention include, but not limited to, nystatin, amphotericin B and the combination thereof.

As used herein, "thickener" means optically acceptable additives that increase viscosity of the formulation. The thickener may make the overall formulation as auris-acceptable viscous fluid when the temperature rises to body temperature. Examples of thickeners that can be used in the present invention include, but not limited to, low-density polyethylene, poloxamers, waxes and the combination thereof. Mineral oil can be added to adjust the viscosity of the thickener. The thickener in the present invention preferably provides a formulation with a viscosity of approximately 70-72,000 cPs at 22.7° C. and about 60-62,000 cPs at 37° C.

As used herein, "injection unit" means a unit that is capable of storing a therapeutic agent and injecting or delivering the therapeutic agent to a target area of a subject. Typical injection units include, but are not limited to, a syringe coupled with a needle or a tube, e.g., via a standard luer lock or luer connector. The needle or tube can be customized as described herein.

As used herein, "flowable" means a fluid having a viscosity less than 100,000 cPs at room temperature.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, special packaging, preservatives, antioxidants and the like. The active pharmaceutical ingredients are considered material.

When a drug is referred to be name herein, all active salts, isomers, and derivatives thereof are considered to be included.

All percentages are by weight, unless indicated otherwise.

BRIEF DESCRIPTION OF THE DRAWINGS

FIGS. 2A-2D are schematic figures showing different designs of the tip of the needle of the therapeutic kit, whereas

DETAILED DESCRIPTION

The present disclosure provides a novel formulation and method for treating ear fungal infections, especially otitis externa, as well as to novel devices for use in said treatments. The formulation and method of the present invention makes it possible to treat and even eradicate the chronic otitis externa by one-time only administration of the formulation to the ear canal.

The disclosure provides a novel formulation for treating fungal ear infection, comprising an antifungal, an antibiotic and an anti-inflammatory agent in a thick base of 60-80,000 cPs at ear or body temperature.

In a preferred embodiment, the disclosure provides a novel formulation for treating fungal ear infection, comprising 0.01% to 1% by weight of a fluoroquinolone, 0.1% to 2% by weight of an azole antifungal, 0.1% to 2% by weight of a thiocarbamate, 0.01% to 2.5% by weight of a corticosteroid, and 50,000 to 200,000 unit/ml of a polyene antifungal; 10% to 70% of thickener, and 30% to 90% of mineral oil. Other therapeutically appropriated base can also be also be utilized in the present invention in place of the thickener without affecting the efficacy of the formulation.

In a preferred embodiment, the fluoroquinolone is selected from the group consisting of: ciprofloxacin, ofloxacin, levofloxacin, gatifloxacin, moxifloxacin and the combination thereof, and more preferably the fluoroquinolone is ciprofloxacin or ofloxacin.

In a preferred embodiment, the triazole antifungal is selected from the group consisting of: clotrimazole, ketoconazole, itraconazole, fluconazole, miconazole, econazole, butoconazole, oxiconazole, sulconazole, terconazole, and the combination thereof, and more preferably the triazole antifungal is clotrimazole, ketoconazole, itraconazole, miconazole or the combination thereof. New generation triazole antifungals include posaconazole and voriconazole can also be used.

In a preferred embodiment, the thiocarbamate antifungal is tolnaftate.

In a preferred embodiment, the corticosteroid is selected from the group consisting of: amcinonide, betamethasone benzoate, betamethasone dipropionate, betamethasone valerate, clobetasol propionate, clocortolone pivalate, desonide, desoximetasone, dexamethasone, dexamethasone sodium phosphate, diflorasone diacetate, fluocinonide, fluocinolone acetonide, flurandrenolide, fluticasone propionate, halcinonide, halobetasol propionate, hydrocortisone, hydrocortisone butyrate, hydrocortisone valerate, mometasone furoate, prednisolone acetate, triamcinolone acetonide, and the combination thereof. More preferably, the corticosteroid is dexamethasone, hydrocortisone, triamcinolone acetonide or the combination thereof.

In a preferred embodiment, the polyene antifungal is nystatin.

In a preferred embodiment, the carrier comprises mineral oil and a thickener. In a particularly preferred embodiment, it comprises 11-21% or 18% paraffin in mineral oil.

In a preferred embodiment, the method for treating ear infection comprises the following step: applying one time a formulation into the ear canal of a mammal, said formulation as described herein, together with thickener and mineral oil; wherein the formulation forms a gel after applying to the ear canal of the mammal, and wherein the gel releases the active ingredients continuously for at least 5 days. In some embodiments, before applying the formulation to the ear canal, the method further comprises the step of debriding infectious and inflammatory debris from the ear canal.

In another embodiment, the invention is a formulation for treating ear infection, comprising: one or more antifungal agents; one or more anti-bacterial agents; one or more anti-inflammatory agents; and a carrier having 40,000-80,000 cPs at 37° C., wherein said carrier retains said active ingredients in an ear for 2-7 days and then egresses or is absorbed.

In a preferred embodiment, the otic formulation, comprises ciprofloxacin, dexamethasone and clotrimazole in an aurally acceptable carrier. Preferably, 0.1-10% ciprofloxacin, 0.1-10% dexamethasone and 0.1-10% clotrimazole are used, most preferred is 0.3% ciprofloxacin, 1% clotrimazole, and 0.1% dexamethasone in a suitable carrier as described herein.

In a preferred embodiment, the suitable mammal that can be treated with the formulation and method of the present invention includes humans, canines, felines, bovines, ovines, porcines, equines, as well as other mammals commonly treated by veterinarians for ear infections.

Figure 1:
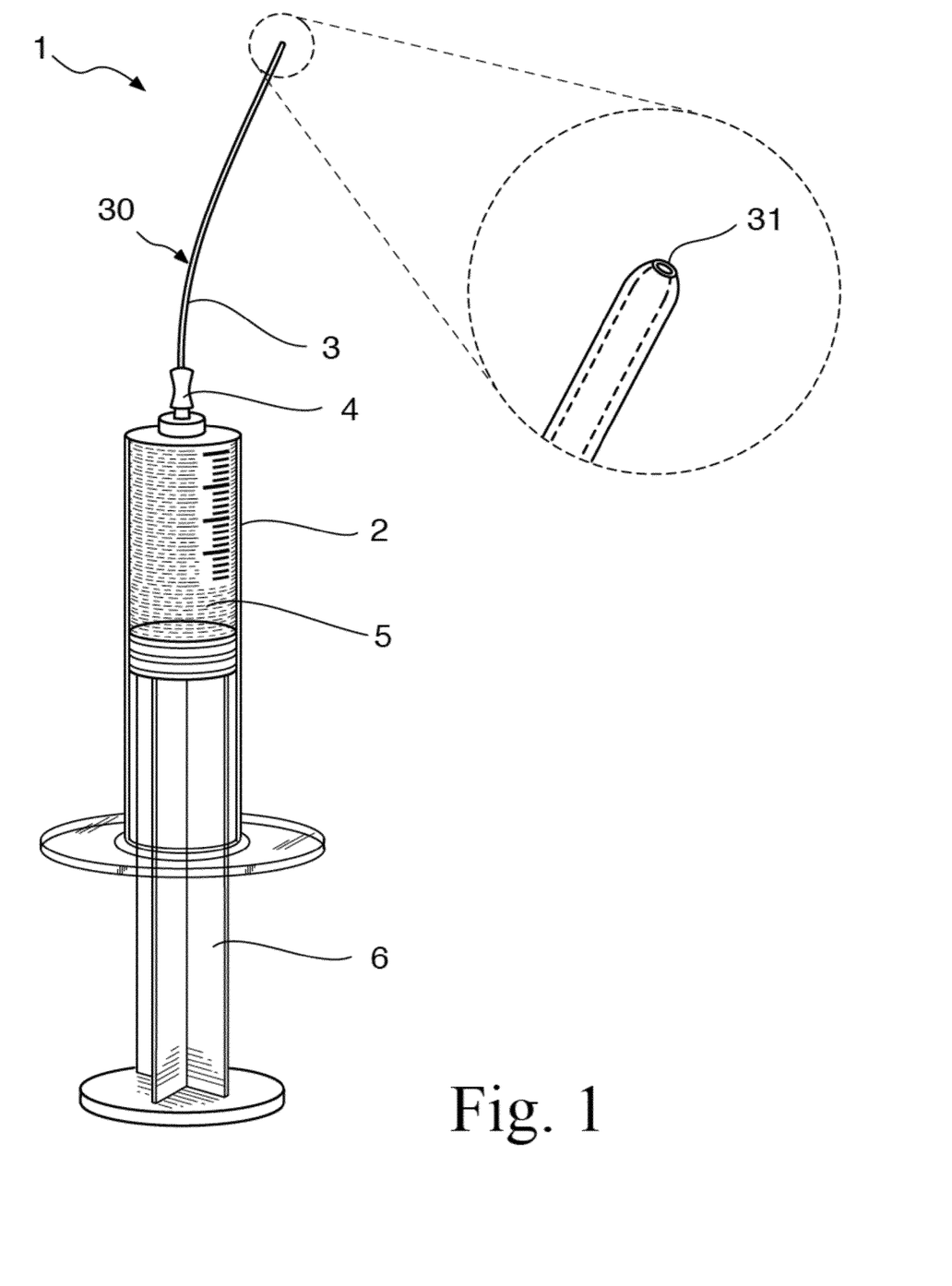
FIG. 1 is a schematic figure showing the therapeutic kit comprising the formulation of the present invention.

The present disclosure further provides a therapeutic kit for treating ear infections. As shown in FIG. 1, the therapeutic kit 1 comprises an injection unit as a syringe, comprising a storage compartment 2 for storing the drug formulation 5 described herein. The storage compartment 2 also has a slidable plunger 6 with handle therein for delivering the drug, wherein the storage compartment 2 is fluidly connected to a delivery unit comprising a needle 3 mounted to the syringe through the cap 4. The needle 3 can have a bend at 30 for the non-linear canal structure. The needle can be bent to any degree suitable for use, as long as it does not affect the dispensation of the therapeutic formulation. The needle 3 can be made of various materials that are acceptable to the field, for example, metal or plastic.

To prevent scratching of sensitive the ear tissues, especially the infected area that is inflamed, the needle 3 is preferably made flexible, especially the distal 1 cm or so thereof. In addition, the needle 3 preferably has a rounded tip 31 as shown in the enlarged circle, thus further preventing scratches.

Figure 2A:
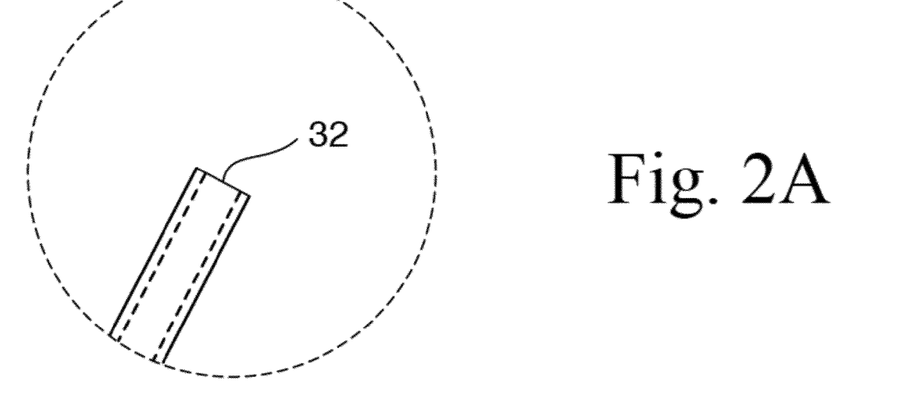
Figure 2B:
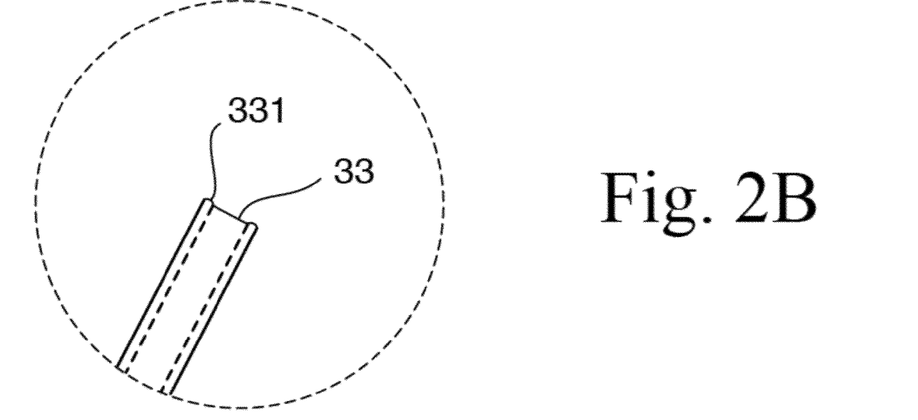
Figure 2C:
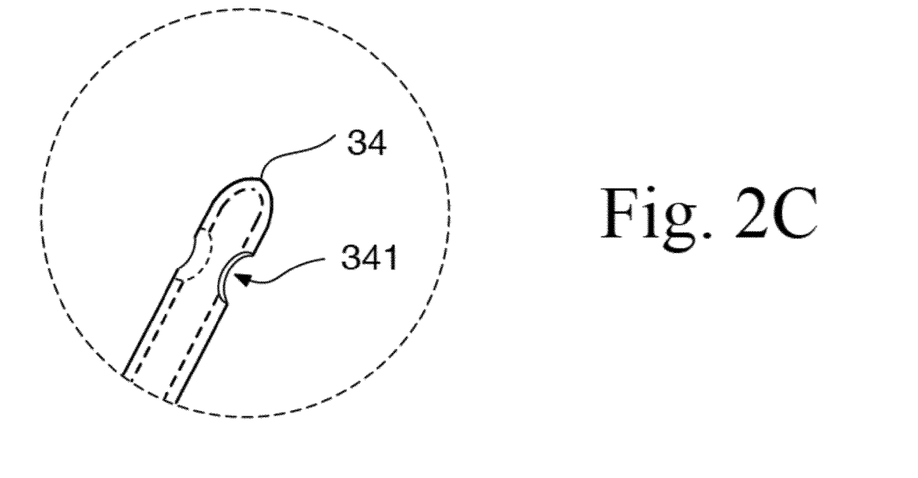
Figure 2D:
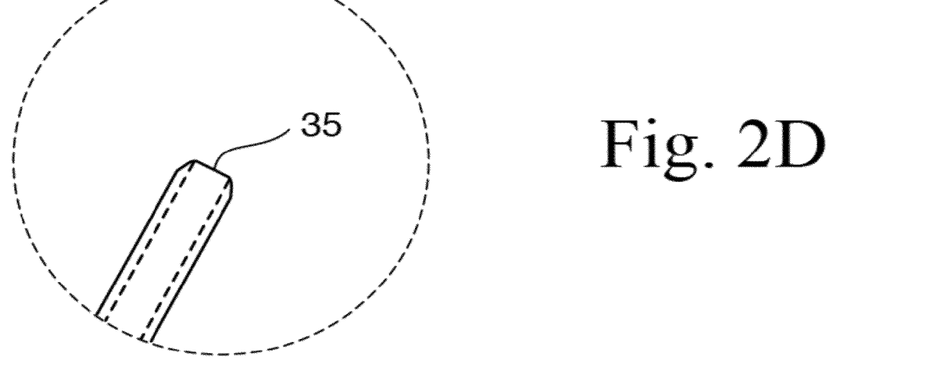
Figure 2E:
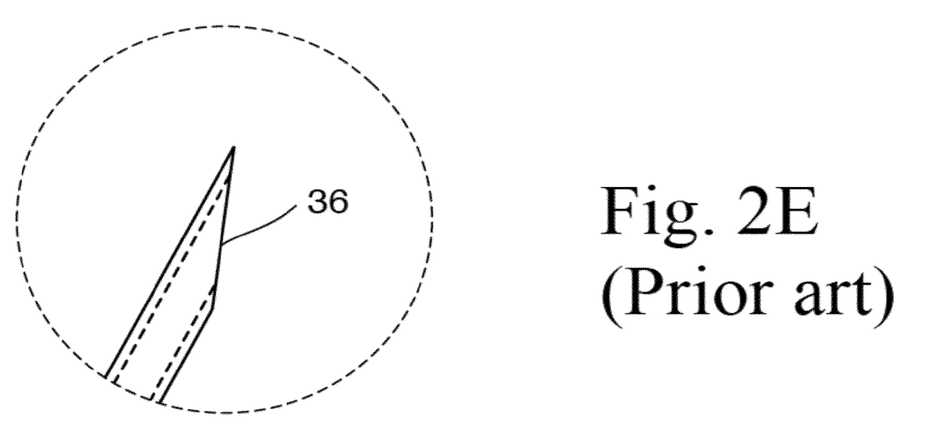
FIG. 2E shows a conventional sharp needle tip.

Different designs of the needle tip are shown in FIGS. 2A-2D. For example, FIG. 2A shows a blunt end 32 of the needle 3. The blunt end 32 is better in this application than the conventional sharp, pointed tip in FIG. 2E because there is no need for the needle to pierce through the skin. A variation of the blunt end is shown in FIG. 2B, where in the blunt end 33 has rounded edge 331, further preventing scratches. Another variation is shown in FIG. 2C, wherein the tip 34 has two dispensing holes 341 at the side surface of the needle instead of the distal end. Or, as shown in FIG. 2D, the needle tip can be made by beveling the edge. Other needle designs can be provided without deviating from the spirit of the present invention.

The entire syringe can be disposable, in which case the storage volume is small to hold the amount suitable for single dosage, for example, 1 to 1.5 ml, in order to prevent waste. Or alternatively, the syringe can be used repeatedly until no therapeutic formulation is left, in which case the storage volume is large to hold multiple dosages, for example 10 to 30 ml, and the needles are single use and disposable. Volumes may change if the patients are not human, e.g., a larger dose may be required for dogs.

Preparing the formulation of the present invention can be performed with various compounding methods, as long as the final product has the desired characteristics, such as remaining flowable at both room temperature and body temperature, while remaining in the ear canal for a prolonged period of time and providing a continuous release of active ingredients.

The following active ingredients are included in the original two formulations making a final product that weighs about 99 grams. The total volume was 99 ml.

| Active Ingredient | Amount |
|---|---|
| Ciprofloxacin powder (0.3%) | 297 mg (0.3 wt %) |
| Nystatin powder (100,000 u/ml approx.) | 1707 mg (100,000 unit/g) |
| Itraconazole or clotrimazole powder (1%) | 990 mg (1%) |
| Dexamethasone powder (0.1%) | 99 mg (0.1 wt %) |
| Tinactin (tolnaftate) 1% solution | 990 mg (1 wt %) |

Ciprofloxacin powder, nystatin powder, itraconazole or clotrimazole powder, dexamethasone powder and tolnaftate powder were measured according to respective weight and placed inside a 200 ml flask.

Nine (9) ml of mineral oil was then added to the flask and mixed well. Finally, approximately 57 ml of thickener (Base, PCCA Plasticized™, from PCCA US, Houston Tex., item code 30-3211) and an additional 28.92 ml of mineral oil was added to the flask make the final volume 99 ml and mixed well. The thickener comprises low density polyethylene and butylated hydroxytoluene, as a stabilizer/antioxidant. Additional mineral oil may be added to adjust the viscosity of the formulation bringing the total volume to more than 99 ml.

These first two original low density polyethylene and butylated hydroxytoluene formulations achieved nearly 100% success rate, but concerns over some of the ingredients were raised with respect to their proprietary nature, so that exact proportions of components were not readily available. Additionally, there was concern that certain ingredients might raise regulatory issues. Therefore, we sought to reformulate the base with the same efficacy and egress characteristics, but that had very benign ingredients in the otic carrier.

We systematically tested mineral oil and a solid paraffin as a thickener, in increasing paraffin ratios, and eventually discovered that a blend of 18% USP (congeals at 56.6° C.) or NF paraffin with USP or NF mineral oil brought to 100% produced a base with excellent characteristics. Ten patients have been tested to date with the new formulation, and all showed 100% cure in 2-8 days, most being cured by 7 days, and with complete egress of the base from the ear. Of course, the percentages of base ingredients can vary depending on the wax chosen, softer waxes needing a higher percentage.

The resulting mixtures were each transparent to a white thick fluid substance. They had viscosity of about 70-72,000 cPs at room temperature. Moderate fluidity was observed, and when the mixture was placed in a syringe, it could be dispensed through an 18-gauge needle with ease. When ambient temperature was raised to 37° C., the viscosity slightly reduced to approximately 60-62,000 cPs.

The average adult human ear canal holds about 0.85 ml of the formulation. However, swollen, erythematous ear canals may only hold 0.2 ml of the formulation. Small children have smaller ear canals. It is expected that a 1 ml dose of formulation is sufficient for most human cases. It is to be noted that the volume may change when the subject is a mammal other than human, and a person of ordinary skilled in the art can easily adjust the amount to suit the treatment needs in other mammals. Different amount of the present formulation may be administered to the mammal's ear canal as readily appreciated by a person skilled in the art.

About 100 patients (work is ongoing and thus the exact number of patients is subject to change) diagnosed with otomycosis, chronic and acute otitis externa were selected for the treatment using the three formulations, ages from 26 months old to 78 years old. The formulations tested are repeated below:

| | |
|---|---|
| Ciprofloxacin | 0.30% |
| | (297 mg) |
| Nystatin | 100,000 units/ml |
| | (1707 mg) |
| Itraconazole | 1% |
| | (990 mg) |
| Dexamethasone | 0.10% |
| | (99 mg) |
| Tolnaftate | 1% |
| | (990 mg) |
| Mineral Oil | ~40% |
| PCCA Plasticizer | ~60% |
| Ciprofloxacin | 0.30% |
| Nystatin | 100,000 units/ml |
| Clotrimazole | 1% |
| | (990 mg) |
| Dexamethasone | 0.10% |
| Tolnaftate | 1% |
| Mineral Oil | ~40% |
| PCCA Plasticizer | ~60% |
| Ciprofloxacin | 0.30% |
| Clotrimazole | 1% |
| Dexamethasone | 0.10% |
| Mineral Oil | ~40% |
| PCCA Plasticizer | ~60% |
| Ciprofloxacin | 0.30% |
| Clotrimazole | 1% |
| Dexamethasone | 0.10% |
| Mineral Oil | 82% |
| Paraffin | 18% |

After debriding the infectious and/or inflammatory debris from the ear canal, an appropriate amount of a formulation from above was administered to the infected ear canal such that all available space in the outer ear was filled. The formulations were stored in a syringe before use, and can be stored at room temperature without deteriorating the therapeutic effect. The syringe is preferably attached to an 18 gauge metal or rigid plastic tip with the distal 1 cm being soft and very flexible to avoid inadvertent injury to the ear drum of outer ear structures. However, other suitable delivery devices can also be used without deviating from the spirit of the present invention.

Figure 3:
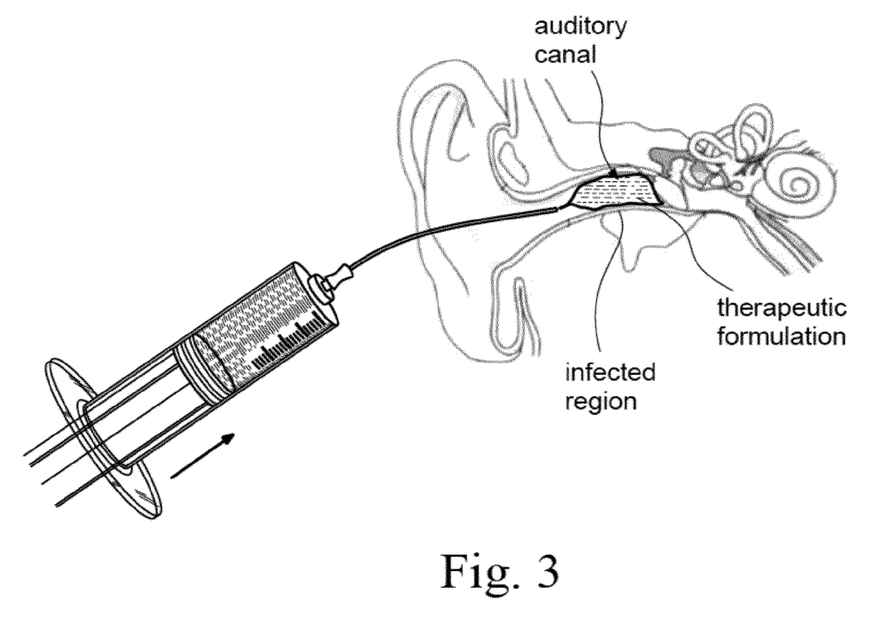
FIG. 3 is a schematic figure showing the method of applying the therapeutic formulation to the infected ear canal of a patient according to the present invention.

The application of the formulation is shown in FIG. 3. First the ENT doctor carefully places the flexible needle inside the patient's auditory canal. Upon pressing the plunger, the therapeutic formulation can be dispensed into the auditory canal and remains therein. Because of the flexible nature and rounded tip of the needle, doctors can minimize possible scratching when applying the therapeutic formulation. The dispensed thick fluid will fill in the space within the auditory canal, thereby contacting the infected area therein while preventing secondary infection in the ear canal.

After administration of the formulation, each patient was examined to ensure that the formulation remained within the ear canal. Cotton balls were provided at the outer ear canal (conchal bowl) to catch egress, but no attempt was made to "plug" the ear canal. Follow-up examination was performed between 7 to 14 days after initial treatment. In several instances, residue of the formulation was observed at day 14, indicating the formulation did maintain within the ear canal for as long as 14 days. Patients reported that symptoms relief occurred usually within three days, while hearing returned to normal within 5 to 7 days after treatment.

Visual examination as well as questionnaire from patients confirmed that no sign of infection existed after day 14 for all patients but two, who also had 98% of symptoms resolved. In other words, the formulation achieved at least 98% cure rate with a single treatment. The formulation of the present invention can continuously release the active ingredient to the infected area, thereby treating as well as preventing proliferation of secondary fungal/bacterial infection that may be caused by the condition within the ear canal occupied by the formulation.

In summary, at least 100 patients have been tested with the above formulations. Only 2 out of 100 patients failed to completely resolve their symptoms and nearly all in 2-4 days. The two patients who failed, required systemic antibiotics and essentially had complicated otitis externa or cellulitis. Further, patients on follow-up are already forming normal cerumen in an incredibly short interval. This is a sign of return to normal epithelial function that is typically not seen for weeks after otitis externa, and may indicate the emollient effects of the mineral oil formulation. It is a notable clinical finding that the inventors have NEVER seen with ear drops of any kind.

We have also tested the formulation on at least 16 cases of bilateral swimmers ear, and are finding the formulation has equivalent efficacy for that infection as well.

We have speculated about the basis for remarkable clinical success of this novel formulation. We believe a previously unstudied synergy is occurring between the components of our product: likely either among the three antifungals—each attacking the fungus in a different way—or between the clotrimazole and ciprofloxacin, as systemic use of other azole antifungals and fluoroquinolones antibiotics have proven synergy.

Future study hinges on randomizing larger numbers of patients to treatment groups with varying combinations of our active pharmaceutical ingredients to prove our theory of synergy. However, published literature on the spectrum of antifungal efficacy suggest that a combination of two or more antifungal agents will provide a broader spectrum of efficacy, and the fact that we have chosen agents with different mechanisms of action suggest that synergy is likely.

| Ingredient | Spectrum of Efficacy |
|---|---|
| Ciprofloxacin | gram positive and gram negative bacteria, including *listeria, Corynebacterium, E. coli, Shigella, Acinetobacter, Bruceila, Sreptococcus agalactiae, Chlamydia, Branhamella, Staphylococcus, Pasteurella, Haemophilus, Enterobacter, Serratia, Hafnia, Salmonella, Citrobacter, Kiebsiella, Edwardsielia, Proteus* (indole-positive andindole-negative), *Providencia,Morganella, Neisseria,Moraxella, Yersinia, Vibrio, Aeromonas, lesiomonas, Campylobacter, Pseudomonas, Legionelia,* and variable activity against *Mycoplasma hominis, Mycobacterium tuberculosis, Mycobacterium fortuitum, Streptococcus viridans, Gardnerella, Flavobacterium, Streptococcus pyogenes, Streptococcus pneumonia, Alcaligenes, Streptococcus faecali.* |
| Clotrimazole | *Aspergillus fiavus, Aspergilius fumigatus, Blastomyces dermatitidis, Candida albicans, Histoplasma capsuiatum, Histoplasma duboisii* |
| Nystatin | primarily fungistatic at low concentrations against biphasic fungi, Dermatophyta and molds, *Candida, Aspergillus* |
| tolnaftate | Fungistatic for dermatophytes and Tinea Versicoior |

The original formulation described above contained five separate active ingredients, and this is preferred as providing the broadest range of activity against multiple species. However, it is expected that a three-ingredient formulation may also prove to be quite effective. Therefore, experiments are planned to systematically test each of the ingredients for synergy with the other ingredients, and such tests will initially be in vitro tests against *Aspergillus niger, Aspergillus flavus, Aspergillus fumigatus, Candida albicans, Candida parapsilosis; Pseudomonas aeruginosa, Staphlococcus aureus, Streptococcus pneumoniae, Haemophilus influenza,* and *Moraxella catarrhalis.* The most suitable formulation can then be clinically tested per FDA requirements.

The most ideal anti-inflammatory may be dexamethasone or hydrocortisone because it is already approved in combination with ciprofloxacin, thus reducing some of the regulatory burden. Hydrocortisone is another option.

Ciprofloxacin may be the most ideal fluoroquinolone because it is a small molecular weight quinolone and more water soluble than others, allowing it to concentrate in the fungal cell membrane in higher amounts than other quinolones. Also, it is the most useful quinolone, since no other quinolones have known activity against *Pseudomonas.*

Because clotrimazole has demonstrated antibacterial activity against *Staphlococcus aureus* and *Pseudomonas* (unlike Nystatin and Tolnaftate), it is the logical choice to include as a third ingredient in either ear gel or drops to improve upon existing drugs for bacterial OE or AOMT.

Most in vitro combination studies have failed to find a significant interaction between fluoroquinolones and antifungal agents, despite in vivo data demonstrating enhancement of antifungal therapy with fluoroquinolone therapy against candidiasis. However, most studies were usually analyzed by the fractional inhibitory concentration index, and Stergiopoulou were able to able to find a significant in vitro synergistic interaction between ciprofloxacin and antifungals against *C. albicans* and *A. fumigatus,* indicating the sensitivity of isobolographic analysis. These authors found that although fluoroquinolones, by themselves do not possess a significant antifungal growth inhibitory activity, when combined with antifungal agents, some antifungal activity is seen, thus demonstrating a synergistic effect.

In more detail, the authors found that synergistic interactions were observed between amphotericin B (0.07-0.31 mg/L) and either ciprofloxacin (0.19-7.65 mg/L) or levofloxacin (0.41-32.88 mg/L) against *C. albicans* and *A. fumigatus.* Synergy also was found between voriconazole (0.09-0.14 mg/L) and ciprofloxacin (0.22-11.41 mg/L) as well as between caspofungin (8.94-22.07 mg/L) and levofloxacin (0.14-5.17 mg/L) against *A. fumigatus.* Some antagonistic interactions were observed between fluoroquinolones and fluconazole against *C. albicans* at higher concentrations. In general, ciprofloxacin enhanced the activity of antifungal agents more than moxifloxacin and levofloxacin against both *C. albicans* and *A. fumigatus.*

The authors speculate on the possible mechanism of action of the synergy seen between these drugs:

1) fluoroquinolones have the capacity to bind to fungal topoisomerase.

2) antifungal agents may alter fungal cell membrane permeability and thereby increase intracellular concentrations of fluoroquinolones.

3) fluoroquinolones may also enhance the activity of antifungal agents by increasing intracellular levels of antifungal agents, as fluoroquinolones are effluxed via ATP-binding cassette (ABC) transporters.

4) fluoroquinolones may also enhance the activity of antifungal agents by increasing the penetration of antifungal agents or increasing the sensitivity of glucan synthase to echinocandins.

In addition to the above synergies, use of more than one agent in a given class is more effective against a broader range of infective agents. Thus, the original 5 (or more) ingredient formulation may have the broadest efficacy.

A limited experiment was performed to demonstrate synergistic effect of the combinations provided herein. The tested strains included 22 *Candida* spp. (5 *C. albicans,* 5 *C. Glabrata,* 5 *C. krusei,* 5 *C. tropicalis,* 1 *C. parapsilosis,* and 1 *C. lusitaniae*) and 10 *Aspergillus* spp. (5 *A. niger,* 5 *A. fumigatus*). These were selected from the Laboratory of Mycology Research isolate collection. These organisms have representative MICs for the species against azoles and included reference QC strains.

96 well round bottom micro well plates were used to prepare checkerboards using the previously reported concentrations of interest both for ciprofloxacin and clotrimazole (4-6). Ciprofloxacin was tested at a range of 0.5-32 mcg/ml and clotrimazole was tested at a range of 0.015-8 mcg/ml. Although checkerboard methodology is not standardized in medical mycology, the drug dilutions, inocula, and plates were prepared using the CLSI M27-A3 (yeasts) and CLSI M38-A1 (moulds) guidelines for antifungal susceptibility testing. Stock solutions were initially diluted in DMSO. Plates were incubated for 48 hours. Readings at the prominent growth reduction endpoints were recorded.

The drug interactions were analyzed by calculating the fractional inhibitory concentration index (FICI) for each strain with the following interpretative guidelines from the Loewe model: Synergy when FICI<0.5 and antagonism when FICI>4 (7).

The experiments were conducted in duplicate for quality control and reproducibility. The second run yielded exact same results as the first run.

The plate set up was as follows:

|   | 1 | 2 | 3 | 4 | 5 | 6 | 7 | 8 | 9 | 10 | 11 | 12 |
|---|---|---|---|---|---|---|---|---|---|----|----|----|
| A | SC | CTZ 0.015 | CTZ 0.03 | CTZ 0.06 | CTZ 0.125 | CTZ 0.25 | CTZ 0.5 | CTZ 1 | CTZ 2 | CTZ 4 | CTZ 8 | GC |
| B | Cipro 32 | CTZ 0.015 Cipro 32 | CTZ 0.03 Cipro 32 | CTZ 0.06 Cipro 32 | CTZ 0.125 Cipro 32 | CTZ 0.25 Cipro 32 | CTZ 0.5 Cipro 32 | CTZ 1 Cipro 32 | CTZ 2 Cipro 32 | CTZ 4 Cipro 32 | CTZ 8 Cipro 32 | GC |
| C | Cipro 16 | CTZ 0.015 Cipro 16 | CTZ 0.03 Cipro 16 | CTZ 0.06 Cipro 16 | CTZ 0.125 Cipro 16 | CTZ 0.25 Cipro 16 | CTZ 0.5 Cipro 16 | CTZ 1 Cipro 16 | CTZ 2 Cipro 16 | CTZ 4 Cipro 16 | CTZ 8 Cipro 16 | GC |
| D | Cipro 8 | CTZ 0.015 Cipro 8 | CTZ 0.03 Cipro 8 | CTZ 0.06 Cipro 8 | CTZ 0.125 Cipro 8 | CTZ 0.25 Cipro 8 | CTZ 0.5 Cipro 8 | CTZ 1 Cipro 8 | CTZ 2 Cipro 8 | CTZ 4 Cipro 8 | CTZ 8 Cipro 8 | GC |
| E | Cipro 4 | CTZ 0.015 Cipro 4 | CTZ 0.03 Cipro 4 | CTZ 0.06 Cipro 4 | CTZ 0.125 Cipro 4 | CTZ 0.25 Cipro 4 | CTZ 0.5 Cipro 4 | CTZ 1 Cipro 4 | CTZ 2 Cipro 4 | CTZ 4 Cipro 4 | CTZ 8 Cipro 4 | GC |
| F | Cipro 2 | CTZ 0.015 Cipro 2 | CTZ 0.03 Cipro 2 | CTZ 0.06 Cipro 2 | CTZ 0.125 Cipro 2 | CTZ 0.25 Cipro 2 | CTZ 0.5 Cipro 2 | CTZ 1 Cipro 2 | CTZ 2 Cipro 2 | CTZ 4 Cipro 2 | CTZ 8 Cipro 2 | GC |
| G | Cipro 1 | CTZ 0.015 Cipro 1.0 | CTZ 0.03 Cipro 1.0 | CTZ 0.06 Cipro 1.0 | CTZ 0.125 Cipro 1.0 | CTZ 0.25 Cipro 1.0 | CTZ 0.5 Cipro 1.0 | CTZ 1 Cipro 1.0 | CTZ 2 Cipro 1.0 | CTZ 4 Cipro 1.0 | CTZ 8 Cipro 1.0 | GC |
| H | Cipro 0.5 | CTZ 0.015 Cipro 0.5 | CTZ 0.03 Cipro 0.5 | CTZ 0.06 Cipro 0.5 | CTZ 0.125 Cipro 0.5 | CTZ 0.25 Cipro 0.5 | CTZ 0.5 Cipro 0.5 | CTZ 1 Cipro 0.5 | CTZ 2 Cipro 0.5 | CTZ 4 Cipro 0.5 | CTZ 8 Cipro 0.5 | GC |

The table below shows the MIC ranges for clotrimazole and ciprofloxacin, as well as the FICI ranges for each of the fungal species tested.

| Species | n | CTZ MIC range (mcg/ml) | CIPRO MIC range (mcg/ml) | FICI range |
|---|---|---|---|---|
| Yeasts | | | | |
| C. albicans | 5 | ≤0.015 | >32 | 2 |
| C. glabrata | 5 | 0.25-1 | >32 | 0.625-1 |
| C. krusei | 5 | 0.06-0.125 | >32 | 1-2 |
| C. tropicalis | 5 | 0.06-2 | >32 | 2 |
| C. parapsilosis | 1 | 0.06 | >32 | 2 |
| C. lusitaniae | 1 | ≤0.015 | >32 | 2 |
| Moulds | | | | |
| A. fumigatus | 5 | 0.25-0.5 | >32 | 2 |
| A. niger | 5 | 0.5-1 | >32 | 2 |

As seen in the table, clotrimazole exhibited a fairly consistent range of MICs for both yeasts and moulds that is compatible with those seen with other azoles. These MICs are below what are easily achievable levels with local concentrations of topical drug. As expected for a non-antifungal, ciprofloxacin exhibited high MICs, which indicate no antifungal activity on its own. As seen on the FICI ranges, all interactions were indifferent, showing no synergy or antagonism. However, some *C. glabrata* and *C. krusei* isolates showed FICIs near 0.5, which may indicate a trend for potential synergy.

This study was limited by the number of isolates. Another caveat is that drug testing ranges were decided based upon previously published synergy studies. Since there was a trend for synergy seen in some isolates of *C. glabrata* and *C. krusei*, it is possible that using higher concentrations of ciprofloxacin may make those interactions significant.

Although there are no established interpretative breakpoints for clotrimazole using CLSI antifungal susceptibility testing methodology, the activity observed is comparable to that of other azoles and the MICs are within the therapeutic range achievable with topical therapy.

The following references are incorporated by reference in their entirety.

1. Narayan S, Swift A. Otitis externa: a clinical review. Br J Hosp Med (Lond). 2011 October; 72(10):554-8.
2. Osguthorpe J D, Nielsen D R. Otitis externa: Review and clinical update. Am Fam Physician. 2006 Nov. 1; 74(9): 1510-6.
3. Rosenfeld R M, Singer M, Wasserman J M, Stinnett S S. Systematic review of topical antimicrobial therapy for acute otitis externa. Otolaryngol Head Neck Surg. 2006 April; 134(4 Suppl):524-48.
4. Stergiopoulou T, Meletiadis J, Sein T, Papaioannidou P, Tsiouris I, Roilides E, et al. Comparative pharmacodynamic interaction analysis between ciprofloxacin, moxifloxacin and levofloxacin and antifungal agents against *Candida albicans* and *Aspergillus fumigatus*. J Antimicrob Chemother. 2009 February; 63(2):343-8.
5. Stergiopoulou T, Meletiadis J, Sein T, Papaioannidou P, Tsiouris I, Roilides E, et al. Isobolographic analysis of pharmacodynamic interactions between antifungal agents and ciprofloxacin against *Candida albicans* and *Aspergillus fumigatus*. Antimicrob Agents Chemother. 2008 June; 52(6):2196-204.
6. Hahn Y H, Ahearn D G, Wilson L A. Comparative efficacy of amphotericin B, clotrimazole and itraconazole against Aspergillus spp. An in vitro study. Mycopathologia. 1993 September; 123(3):135-40.
7. Johnson M D, MacDougall C, Ostrosky-Zeichner L, Perfect J R, Rex J H. Combination antifungal therapy. Antimicrob Agents Chemother. 2004 March; 48(3):693-715.
8. Munguia et al., *Ototopical antifungals and otomycosis: A review*, International J. of Pediatric Otorhinolaryngology (2008) 72, 453-459.
9. Robert Sander, *Otitis Externa: A practical Guide to Treatment and Invention*, Am. Fam. Physician., 2001 Mar. 1; 63(5):927-937.
10. U.S. Pat. No. 7,220,431 & U.S. Pat. No. 8,030,297

While preferred embodiments of the present invention have been shown and described herein, such embodiments are provided by way of example only. Various alternatives to the embodiments can be optionally employed without deviating from the spirit of the present invention. The scope of the invention is defined by the following claims.

What is claimed is:

1. A formulation for treating ear infection, comprising:
   a) active ingredients for treating fungal and bacterial infections, comprising:
      i) a fluoroquinolone;
      ii) a triazole antifungal;
      iii) a thiocarbamate antifungal;
      iv) a corticosteroid; and
      v) a polyene antifungal, and
   b) a carrier;
   wherein said formulation is capable of delivery to the ear canal of a mammal in a flowable fluid form, and
   wherein said carrier includes at least one thickener so that upon introduction into the ear canal the formulation remains in the ear canal for at least 3 days releasing said active ingredients.

2. The formulation of claim 1, wherein said carrier comprises: about 10-90% of said thickener.

3. The formulation of claim 1, wherein said carrier comprises 10% to 90% of said thickener; and 30% to 70% of mineral oil.

4. The formulation of claim 1, wherein said carrier comprises 75-90% mineral oil and 10% to 25% of wax.

5. The formulation of claim 1, wherein said carrier comprises 82% of said mineral oil and 18% of paraffin.

6. The formulation of claim 1, wherein said formulation comprises 0.01% to 1% by weight of said fluoroquinolone that is selected from the group consisting of: ciprofloxacin, ofloxacin, levofloxacin, norfloxacin, gatifloxacin, gemifoxacin, moxifloxacin and combinations thereof.

7. The formulation of claim 6, wherein said fluoroquinolone is ciprofloxacin, ofloxacin or the combination thereof.

8. The formulation of claim 1, wherein said formulation comprises 0.1% to 2% by weight of said triazole antifungal that is selected from the group consisting of: clotrimazole, ketoconazole, itraconazole, fluconazole, miconazole, econazole, butoconazole, oxiconazole, sulconazole, terconazole, and the combination thereof.

9. The formulation of claim 8, wherein said triazole antifungal is clotrimazole, ketoconazole, itraconazole, miconazole and the combination thereof.

10. The formulation of claim 1, wherein said formulation comprises 0.1% to 2% by weight of said thiocarbamate antifungal that is tolnaftate.

11. The formulation of claim 1, wherein said formulation comprises 0.01% to 2.5% by weight of said corticosteroid that is selected from the group consisting of: amcinonide, betamethasone benzoate, betamethasone dipropionate, betamethasone valerate, clobetasol propionate, clocortolone pivalate, desonide, desoximetasone, dexamethasone, dexamethasone sodium phosphate, diflorasone diacetate, fluocinonide, fluocinolone acetonide, flurandrenolide, fluticasone propionate, halcinonide, halobetasol propionate, hydrocortisone, hydrocortisone butyrate, hydrocortisone valerate, mometasonefuroate, prednisolone acetate, triamcinolone acetonide, and the combination thereof.

12. The formulation of claim 11, wherein said corticosteroid is dexamethasone, hydrocortisone, triamcinolone acetonide or the combination thereof.

13. The formulation of claim 1, wherein said formulation comprises 50,000 to 200,000 unit/ml of said polyene antifungal, wherein said polyene antifungal is nystatin.

14. The formulation of claim 1, wherein said formulation has a viscosity of about 62,000 cPs at 37° C.

15. A formulation for treating ear infection, comprising:
   a) active ingredients for treating fungal and bacterial infection comprising:
      i) about 0.3% by weight of ciprofloxacin, ofloxacin, or the combination thereof;
      ii) about 1% by weight of a clotrimazole, itraconazole, or the combination thereof;
      iii) about 1% by weight of a tolnaftate;
      iv) about 0.1% by weight of a dexamethasone; and
      v) about 100,000 unit/ml of a nystatin;
   b) about 10-25% of wax; and
   c) about 75-90% of mineral oil;
   d) wherein after applying to the ear canal of a mammal having said ear infection, said formulation remains in the ear canal and has a viscosity of about 62,000 cPs at 37° C.; and
   e) wherein upon introduction into the ear canal said formulation remains in the ear canal releasing said active ingredients for 2-7 days, and thereafter is not found in said ear, and
   f) wherein said formulation is for single treatment and has a cure rate of at least 95%.

16. A formulation for treating ear infection, comprising
   a) one or more antifungal agents;
   b) one or more anti-bacterial agents;
   c) one or more anti-inflammatory agents; and
   d) a carrier having 40,000-80,000 cPs at 37° C., wherein said carrier retains said active ingredients in an ear for 2-7 days and then egresses or is absorbed,
   wherein said formulation is for single treatment and has a cure rate of at least 95%.

17. An otic formulation, comprising ciprofloxacin, dexamethasone and clotrimazole in an aurally acceptable carrier, said carrier having 40,000-80,000 cPs at 37° C., wherein said carrier retains said active ingredients in an ear for 2-7 days and then egresses or is absorbed, wherein said formulation is for single treatment and has a cure rate of at least 95%.

18. An otic formulation, selected from:
   0.01% fluoroquinolone, 0.1% triazole antifungal, 0.1% thiocarbamate,
   0.01% corticosteroid, and 50,000 unit/ml of a polyene antifungal plus thickener and mineral oil;
   1% fluoroquinolone, 2% triazole antifungal, 2% thiocarbamate, 1% by weight of a corticosteroid, and 200,000 unit/ml of a polyene antifungal in thickener, and mineral oil;
   0.3% ciprofloxacin, 1% clotrimazole, 1% tolnaftate, 0.1% dexamethasone; and 100,000 unit/ml of a nystatin in an otic carrier that is 10-25% wax, and 75-90% of mineral oil;
   0.3% ciprofloxacin, 1% ofloxacin, 1% itraconazole, 1% tolnaftate 0.1% dexamethasone, and 100,000 unit/ml of a nystatin in 10-25% wax and 75-90% mineral oil;
   0.3% ciprofloxacin, 1% ofloxacin, 1% itraconazole, 1% tolnaftate, 0.1% dexamethasone, and 100,000 unit/ml of nystatin in 55-60% PCCA Plasticized™ and 40-45% mineral oil;
   0.3% ciprofloxacin, 1% ofloxacin, 1% clotrimazole, 1% tolnaftate 0.1% dexamethasone, and 100,000 unit/ml of a nystatin in 55-60% PCCA Plasticized™ and 40-45% mineral oil;
   0.3% ciprofloxacin ofloxacin or the combination thereof, 1% by weight of a clotrimazole, itraconazole, or the combination thereof; 1% by weight of a tolnaftate; 0.1% by weight of a dexamethasone; and 100,000 unit/ml of a nystatin in an otic carrier that is 10-25% of wax; and 75-90% of mineral oil;
   0.3% ciprofloxacin, 100,000 u/ml Nystatin, 1% Itraconazole, 0.1% Dexamethasone and 1% Tolnaftate in 18% candela wax and 82% mineral oil;

0.3% ciprofloxacin; 100,000 u/ml Nystatin, 1% clotrimazole, 0.1% Dexamethasone, 1% Tolnaftate (1%) in 80% mineral oil and 20% bees wax;

0.3% ciprofloxacin; 100,000 u/ml Nystatin, 1% clotrimazole, 0.1% Dexamethasone, 1% Tolnaftate in 82% mineral oil and 18% paraffin;

0.3% ciprofloxacin; 100,000 u/ml Nystatin, 1% clotrimazole, 0.1% Dexamethasone, 1% Tolnaftate in mineral oil and wax;

0.3% ciprofloxacin; 1% clotrimazole, 0.1% Dexamethasone in 82% mineral oil and 18% paraffin;

0.5% ciprofloxacin; 2% clotrimazole, 0.2% Dexamethasone in 82% mineral oil and 18% paraffin;

0.6% ciprofloxacin; 2% clotrimazole, 0.2% Dexamethasone in 82% mineral oil and 18% paraffin;

0.3% ciprofloxacin, 100,000 u/ml Nystatin, 0.1% dexamethasone;

0.3% ciprofloxacin, 1% voriconazole, 0.1% dexamethasone;

0.3% ciprofloxacin, 1% amphotericin B, 0.1% dexamethasone;

0.3% levofloxacin, 1% amphotericin B, 0.1% dexamethasone;

0.3% levofloxacin, 1% voriconazole, 0.1% dexamethasone;

0.3% ciprofloxacin, 1% ketoconazole, 0.1% dexamethasone; and 0.3% Ciprofloxacin; 1% clotrimazole, 0.1% hydrocortisone.

19. A method for treating ear infection, comprising applying a single dose of the formulation as in one of claim 1-18 into the ear canal of a mammal with an ear infection.

20. A therapeutic kit, comprising an injection unit comprising a storage compartment fluidly coupled to a delivery component, and a therapeutic formulation of claim 1 stored within said storage compartment, and wherein said delivery component comprises disposable needles having a 5-15 degree bend and a rounded tip.

* * * * *